(12) United States Patent
Sova

(10) Patent No.: US 10,111,800 B2
(45) Date of Patent: Oct. 30, 2018

(54) THERAPEUTIC BOARD FOR TREATMENT OF THE SPINE

(71) Applicant: J. Christopher Sova, Monroe, CT (US)

(72) Inventor: J. Christopher Sova, Monroe, CT (US)

( * ) Notice: Subject to any disclaimer, the term of this patent is extended or adjusted under 35 U.S.C. 154(b) by 575 days.

(21) Appl. No.: 14/735,550

(22) Filed: Jun. 10, 2015

(65) Prior Publication Data

US 2015/0351989 A1    Dec. 10, 2015

Related U.S. Application Data

(60) Provisional application No. 62/009,971, filed on Jun. 10, 2014.

(51) Int. Cl.
*A61H 1/02* (2006.01)
*A61F 5/02* (2006.01)
*A61H 1/00* (2006.01)

(52) U.S. Cl.
CPC ........... *A61H 1/0218* (2013.01); *A61F 5/024* (2013.01); *A61H 1/02* (2013.01); *A61H 1/0222* (2013.01); *A61H 1/0292* (2013.01); *A61H 1/0296* (2013.01); *A61H 1/008* (2013.01); *A61H 2001/0203* (2013.01); *A61H 2201/0192* (2013.01); *A61H 2201/1261* (2013.01); *A61H 2201/1284* (2013.01); *A61H 2201/168* (2013.01); *A61H 2201/1623* (2013.01); *A61H 2201/1647* (2013.01); *A61H 2201/1685* (2013.01); *A61H 2201/1695* (2013.01); *A61H 2203/0456* (2013.01)

(58) Field of Classification Search
CPC .......... A61H 1/00; A61H 1/02; A61H 1/0218; A61H 1/0222; A61H 1/0292; A61H 1/0296; A61H 2001/0203; A61H 2001/0207; A61H 2201/0192; A61F 5/01; A61F 5/0102; A61F 5/0193; A61F 5/02; A61F 5/024; A61F 5/026; A61F 5/028; A61F 5/048; A61F 5/03; A63B 23/02; A63B 23/0233; A63B 23/0238
USPC ..... 606/240, 241; 602/5, 18, 19, 32, 33, 35; 2/467; 601/115, 122, 116, 128, 133, 134, 601/136, 138, 145, 146
See application file for complete search history.

(56) References Cited

U.S. PATENT DOCUMENTS

| | | | | |
|---|---|---|---|---|
| 4,233,966 | A | * | 11/1980 | Takahashi .............. A61H 39/04 601/134 |
| 4,923,187 | A | * | 5/1990 | Mombrinie .......... A61B 6/0442 5/601 |
| 5,007,414 | A | * | 4/1991 | Sexton ...................... A61F 5/01 602/19 |
| 5,360,392 | A | * | 11/1994 | McCoy ..................... A61F 5/02 5/621 |

(Continued)

*Primary Examiner* — Colin W Stuart
(74) *Attorney, Agent, or Firm* — Dunlap Bennett & Ludwig PLLC

(57) ABSTRACT

A therapeutic device is provided. The therapeutic device includes a substantially flat board and a pair of risers. The board includes an upper surface, a lower surface opposite the upper surface, and a perimeter comprising a top edge and a bottom edge opposite the top edge. A first riser and a second riser protrude from the top surface of the board. Each of the first riser and the second riser include a taper from a first end to a second end. The first end of the first riser and the first end of the second riser are disposed near the top edge. The first and second risers are disposed at an acute angle relative to one another.

9 Claims, 5 Drawing Sheets

(56) References Cited

U.S. PATENT DOCUMENTS

| | | | | |
|---|---|---|---|---|
| 5,820,573 A | * | 10/1998 | Ramos | A61H 7/001 601/134 |
| 6,921,372 B2 | * | 7/2005 | Shin | A61F 5/01 5/630 |
| 8,696,607 B2 | * | 4/2014 | McDonnell | 128/845 |

* cited by examiner

THERAPEUTIC BOARD FOR TREATMENT OF THE SPINE

CROSS-REFERENCE TO RELATED APPLICATION

This application claims the benefit of priority of U.S. provisional application No. 62/009,971, filed Jun. 10, 2014, the contents of which are herein incorporated by reference.

BACKGROUND OF THE INVENTION

The present invention relates to a therapeutic device and, more particularly, to a therapeutic board for treatment of the spine.

Scoliosis is a medical condition in which a person's spinal has a three-dimensional deviation. Although it is a complex three-dimensional condition, on an X-ray the spine of an individual with scoliosis can resemble an "S" or a "?", rather than a straight line. There is no therapeutic treatment/correction of scoliosis other than exercises, braces and surgery. Further, the current methods for correcting poor posture are ineffective and cumbersome, with poor compliance.

As can be seen, there is a need for a therapeutic device to treat scoliosis and bad posture.

SUMMARY OF THE INVENTION

In one aspect of the present invention, a therapeutic device comprises: a board having an upper surface, a lower surface opposite the upper surface, and a perimeter comprising a top edge and a bottom edge opposite the top edge; and a first riser and a second riser protruding from the top surface of the board, each comprising a first end and a second end, wherein a taper is formed from the first end to the second end, wherein the first riser and the second riser are disposed at an acute angle relative to one another.

These and other features, aspects and advantages of the present invention will become better understood with reference to the following drawings, description and claims.

DETAILED DESCRIPTION OF THE INVENTION

Figure 1:
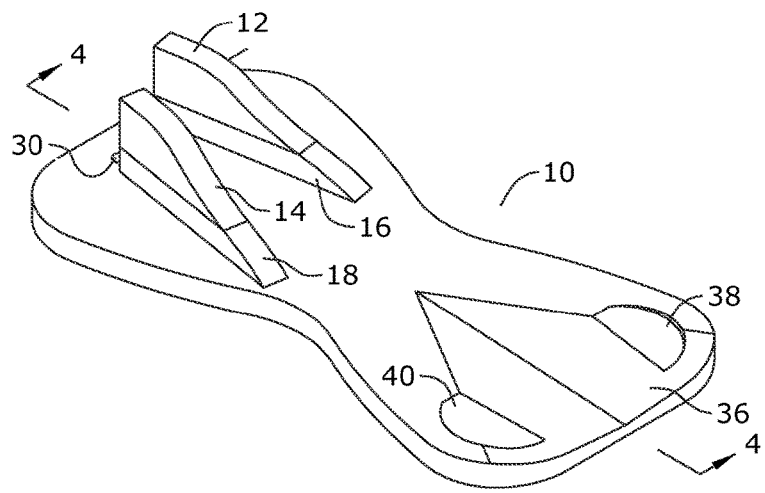
FIG. 1 is a perspective view of an embodiment of the present invention illustrated in an exemplary arrangement.
Figure 2:
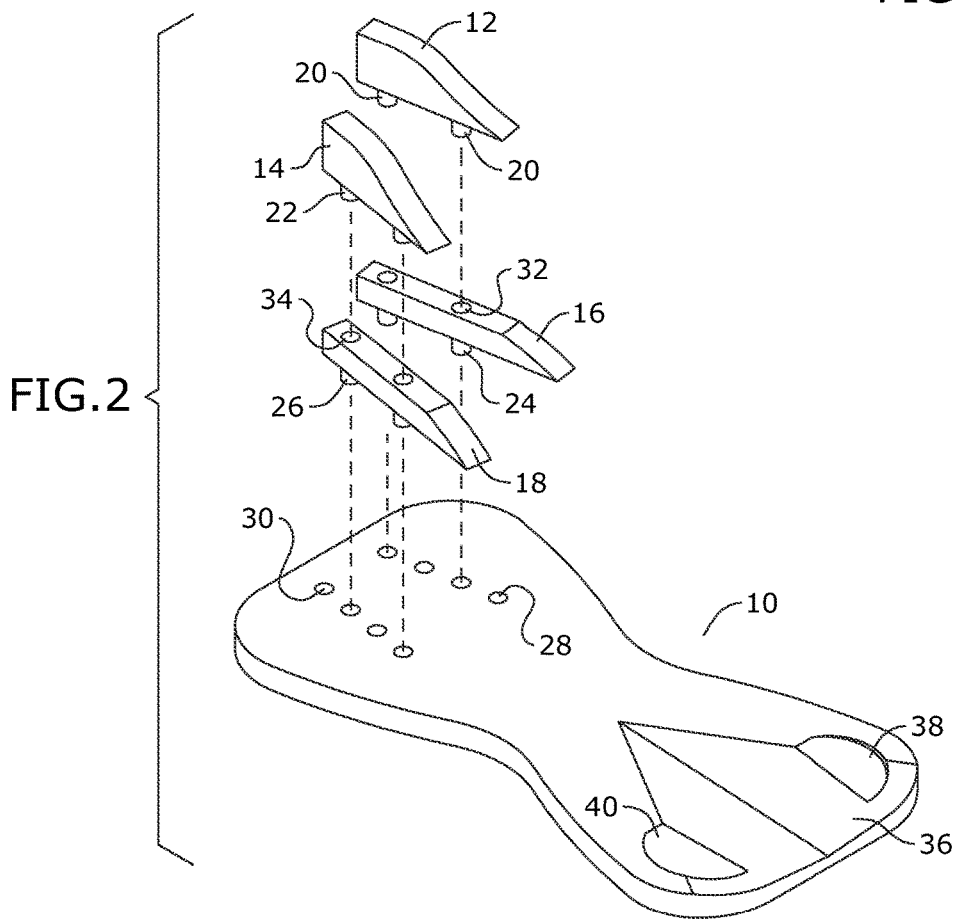
FIG. 2 is an exploded view of an embodiment of the present invention.
Figure 3:
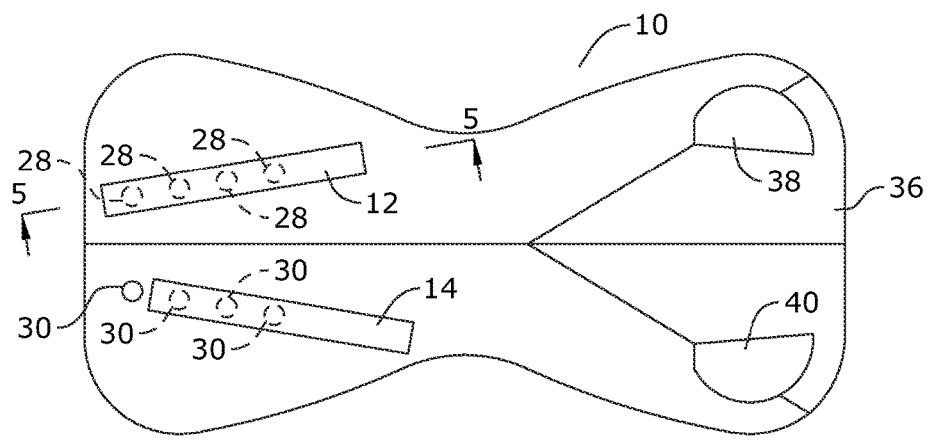
FIG. 3 is a top view of an embodiment of the present invention.
Figure 4:
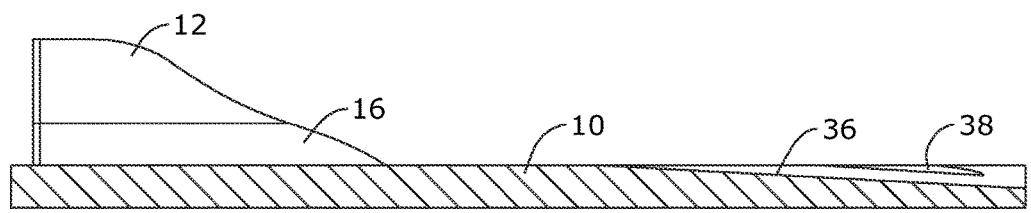
FIG. 4 is a section view of the present invention taken along line 4-4 in FIG. 1.
Figure 5:
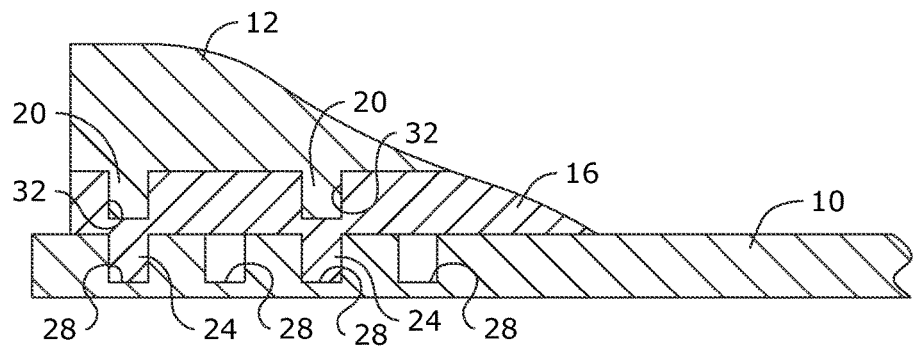
FIG. 5 is a section view of the present invention taken along line 5-5 in FIG. 3.
Figure 6:
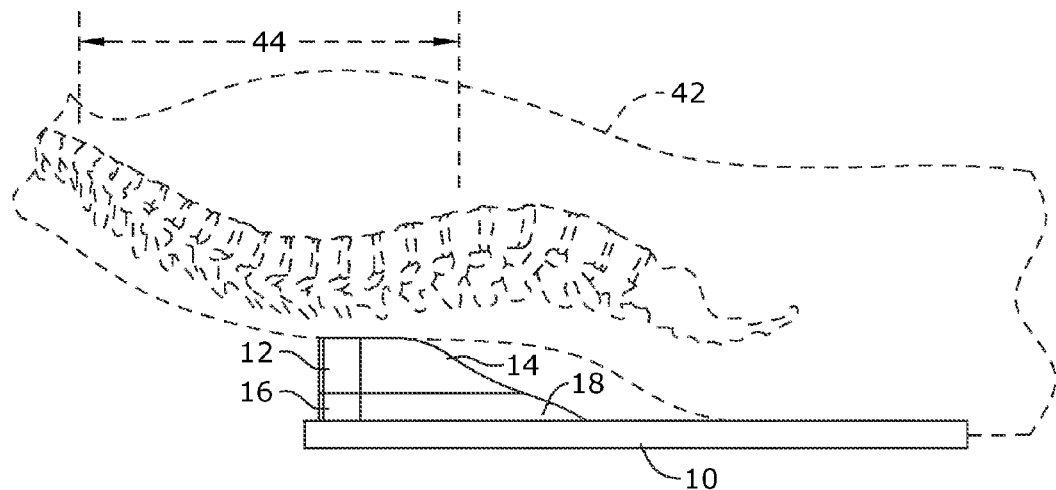
FIG. 6 is a side view of the present invention illustrating an exemplary position of the patient beginning to use the device.
Figure 7:
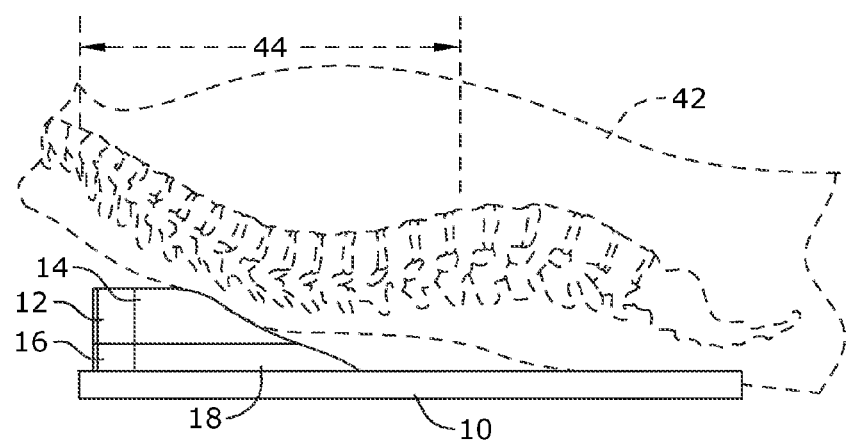
FIG. 7 is a side view of the present invention illustrating an exemplary position of the patient as the use progresses.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention includes an apparatus which treats and corrects scoliosis and poor posture. The therapeutic board of the present invention aligns, de-rotates and straightens the spine for people with scoliosis and corrects poor posture allowing natural extension. For the correction of scoliosis, by offsetting the risers and using one's own body weight, the present invention is used to de-rotate (untwist) the spine and thus straightening the spine. Each individual thoracic vertebral segment is stretched into extension, elongating the ventral aspects of the thoracic spine thus affecting long term straightening and flexibility of the thoracic spine. For people with poor posture, the spine is pushed into extension thus allowing more flexibility and stretches the ventral aspects of the thoracic spine by allowing movement of the facet joints and stretching the ligaments at each thoracic vertebral segment.

The present invention includes a board including two matching sloping risers with pegs on the bottom that insert into holes in the board. The risers may be disposed on the board equidistant and at an acute angle to one another to form a "V" shape. A spacer may be added under the riser to increase the height of the risers. The present invention can be made of wood or molded resin.

With scoliosis, rotation is accompanied with lateral bending. When one riser if offset to the other (one closer to the top edge than the other) laying on the board causes the spine to de-rotate, which allows for straightening the curve caused by scoliosis. This de-rotation is performed at each individual vertebral level by sliding down the board. For example, in people with a "rib-hump" on the right, the right riser is closer to the top edge causing de-rotation of the spine to the left. The biomechanical coupling inherent in the spine in people with scoliosis is directly addressed. While the board is important to align the patient over the risers, the board holds the risers securely in place to carefully and accurately insure the risers are at the desired vertebral level. The risers push into the thoracic spine at the desired vertebral levels bilaterally thus allowing the spine to extend. The risers affect movement of the facet joints, ligaments, discs and muscles of the thoracic spine. The spacers can be used to further increase the vertical dimension of the risers.

Referring to FIGS. 1 through 10, the present invention includes a therapeutic device including a substantially flat board 10. The board 10 includes an upper surface, a lower surface opposite the upper surface, and a perimeter including a top edge and a bottom edge opposite the top edge. A first riser 12 and a second riser 14 protrude from the top surface of the board 10 and are side by side. Each of the first riser 12 and the second riser 14 include a taper from a first end to a second end. The first end of the first riser 12 and the first end of the second riser 14 are disposed near the top edge.

The first end of the first riser 12 and the first end of the second riser 14 are closer together than the second end of the first riser 12 and the second end of the second riser 14. Therefore, the first and second risers 12, 14 are disposed at an acute angle relative to one another.

The risers 12, 14 of the present invention may be releasably attachable to the upper surface of the board via a plurality of mating connectors. In such embodiments, the first riser 12 may include pegs 20 and the second riser 14 may include pegs 22. The pegs 22, 20 may fit and secure within peg holes 28, 30. The first riser peg holes 28 may form an angle relative to the second riser peg holes 30. In certain embodiments, each the first and second riser peg holes 28, 30 may include a row of four peg holes 28, 30. Each of the first and second risers 12, 14 may include two pegs 20, 22. Therefore, the pegs 20, 22 of the first and second risers 12, 14 may be placed in different peg holes 28, 30 to adjust the distance between the first ends of the first and second risers 12, 14 and the top edge.

Figure 8:
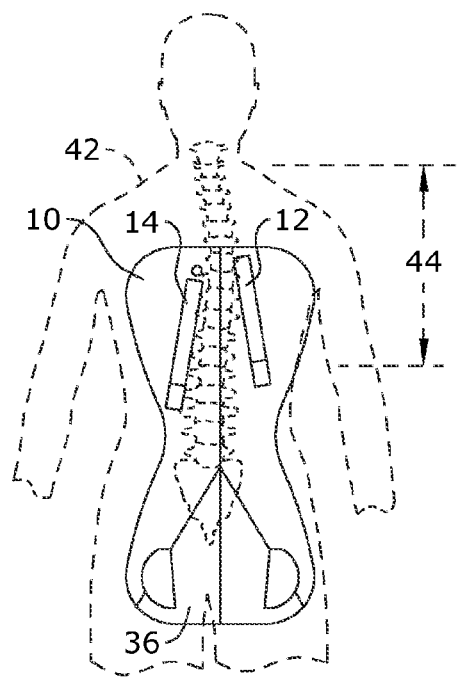
FIG. 8 is a schematic view of the present invention, illustrating an exemplary position of a patient with a convex right scoliosis when risers are offset to produce left rotation of the vertebral body.
Figure 9:
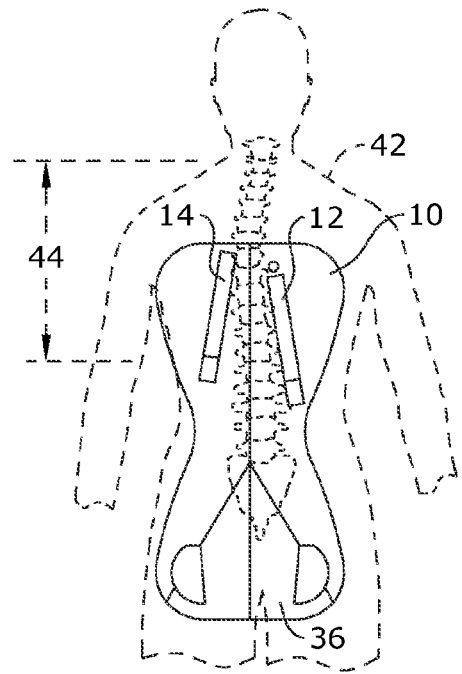
FIG. 9 is a schematic view of the present invention, illustrating an exemplary position of a patient with a convex left scoliosis when risers are offset to produce right rotation of the vertebral body.
Figure 10:
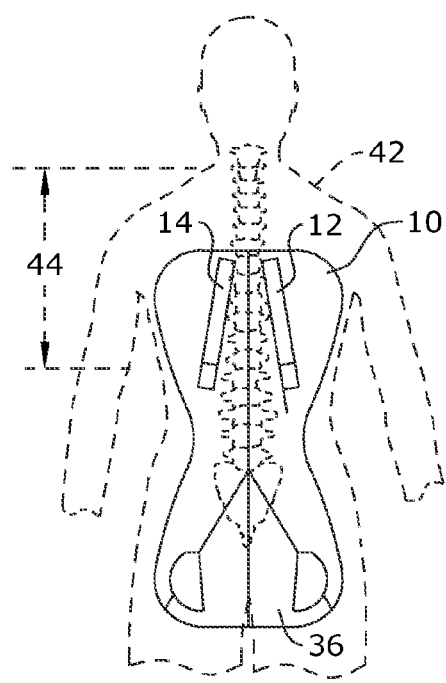
FIG. 10 is a schematic view of the present invention, illustrating an exemplary position of a patient when the risers are aligned for posture correction.

As illustrated in FIGS. 8 through 10, the above configuration allows the first and second risers 12, 14 to be adjustable between a first position and a second position. The first position includes the first ends of the risers 12, 14 being equidistant from the top edge of the board 10, forming a V-shape. The second position includes the first end of the first riser 12 disposed closer to the top edge of the board than the first end of the second riser 14 and vice versa forming an offset V-shape. The offset second position may be used for the treatment of scoliosis and is operable to straighten the thoracic curve section 44 of the spine. The aligned V-shape first position may be used for the treatment of poor posture.

The present invention may further include spacers 16, 18. The spacers 16, 18 may adjust the height of the risers 12, 14. For example, the present invention may include a first spacer 16 and a second spacer 18 with a top and a bottom. The top of the first spacer 16 may include peg holes 32 to receive pegs 20 formed at the bottom of the first riser 12. The bottom of the first spacer 16 may include pegs 24 that are formed to fit within the peg holes 28 formed on the board 10. The top of the second spacer 18 may include peg holes 34 to receive pegs 22 formed at the bottom of the second riser 12. The bottom of the second spacer 18 may include pegs 26 that are formed to fit within the peg holes 30 formed on the board 10.

In certain embodiments, the board 10 may include a beveled portion 36 that tapers towards the bottom edge. The beveled portion 36 allows the user 42 to slide easily along the board 10 during use. The present invention may also include a first handle aperture 38 and a second handle apertures 40. The handle apertures 38, 40 may be formed through the board near the bottom edge. The handle apertures 38, 40 allow users 42 to easily grasp and transport the present invention.

Figure 11:
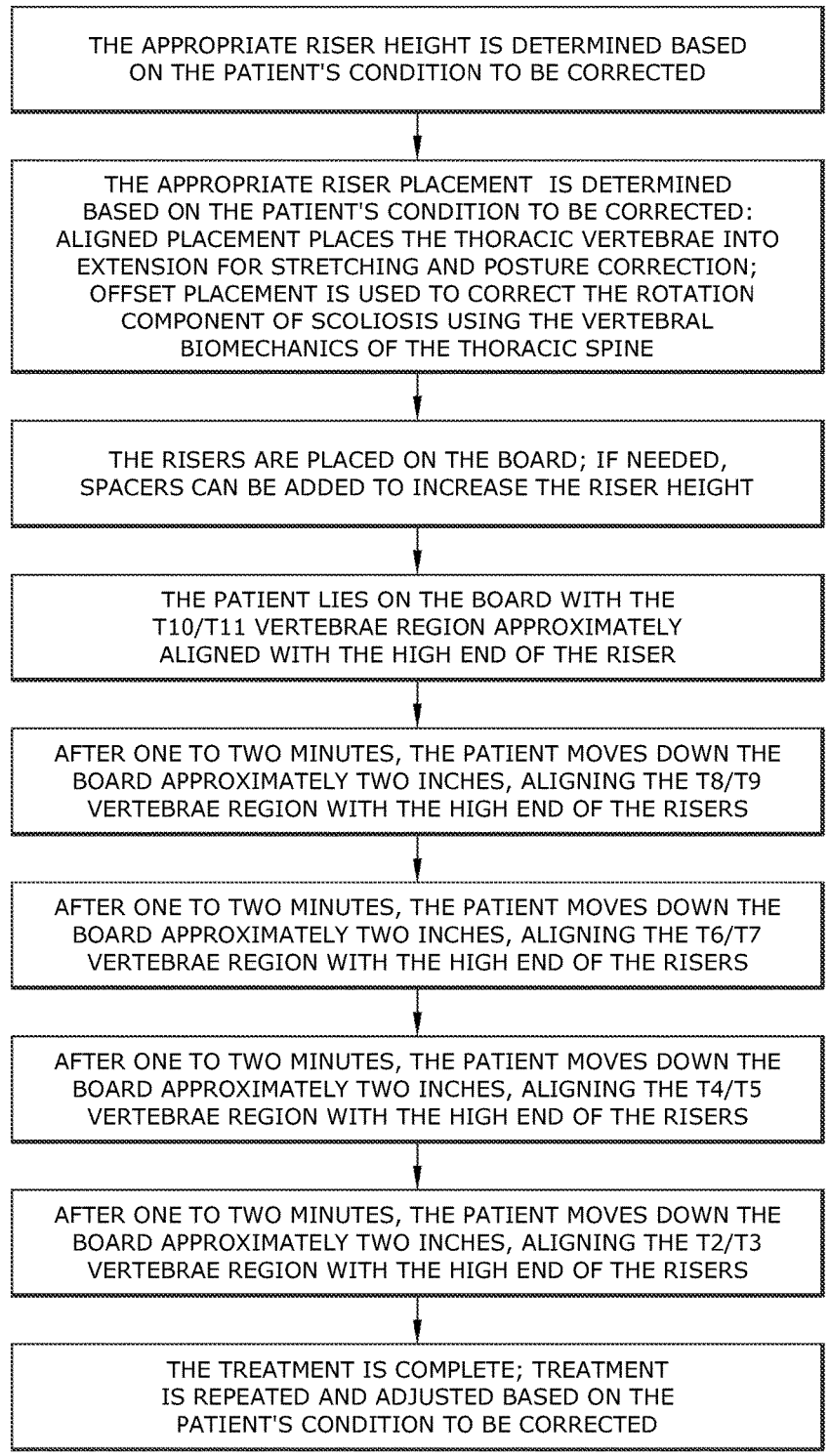
FIG. 11 is a flow chart of a method of using the present invention.

Referring to FIG. 11, a method of the present invention may include the following. The appropriate riser height may be determined based on the patient's condition to be corrected. The spacers may be used to increase the height. The appropriate riser placement may be determined based on the patient's condition to be corrected. The patient lies on the board with T10/T11 vertebrae aligned with the high end of the riser. After one to two minutes, the patient moves down the board approximately two inches, aligning the T8/T9 vertebrae region with the high end of the risers. After one to two minutes, the patient moves down the board approximately two inches, aligning the T6/T7 vertebrae region with the high end of the risers. After one to two minutes, the patient moves down the board approximately two inches, aligning the T4/T5 vertebrae region with the high end of the risers. After one to two minutes, the patient moves down the board approximately two inches, aligning the T2/T3 vertebrae region with the high end of the risers. The treatment may then be complete. The treatment may be repeated and adjusted based on the patient's condition to be corrected.

The present invention re-aligns the spine from lateral flexion and rotation, to straight and elongated. Also inherent in the invention is increasing spinal flexibility and improved muscle tone due to a more balanced spine, front to back, side to side, top to bottom. The procedure may be performed around three times per week and may make permanent and positive changes to the thoracic spine. If both risers are equidistant from the end of the board, it is used to correct posture, specifically hyperkyphosis and forward head carriage. This is extremely helpful in those whose job is to sit most days at a computer screen. The present invention can be used in the geriatric population to help maintain an erect stature. In this manner, the present invention can aid in an increased lung capacity and other organs in the chest encased by ribs in the front and back and the spine. The present invention is portable, easy to use and is may be used at home, thus decreasing the need for visits to chiropractic or physical therapy sessions for the specific conditions mentioned above.

A method of making the present invention may include the following. Patterns of both the board and risers may first be produced. The board is a standard size, although a pediatric version may be also available. The risers may be in different sizes, such as from about 4" to about 9" long, and from about 2" to about 5" high. The slopes may vary depending of the length of the risers. The shorter and higher the riser is, the greater the affect it has on the spine and the lower and longer the riser is, the lesser the effect it has on the spine. The longer and lower risers can be used in the geriatric population. The board pattern may be suited to accommodate varying body sizes and shapes. Also, the board accommodates for the anatomy, i.e. the sacrum. The board has two rows of four holes each, equidistant and at acute angles to each other. The holes in the board are to accommodate the risers and the risers directly affect the spine. When the patterns are made, the product can be cut out of wood or from molded resin. Holes are to be drilled into the board and routed. The risers are drilled to accommodate the dowels that protrude from the bottom.

It should be understood, of course, that the foregoing relates to exemplary embodiments of the invention and that modifications may be made without departing from the spirit and scope of the invention as set forth in the following claims.

What is claimed is:

1. A therapeutic device comprising:
   a board having an upper surface, a lower surface opposite the upper surface, and a perimeter comprising a top edge and a bottom edge opposite the top edge; and
   a first riser and a second riser protruding side by side from the upper surface of the board, each of the first riser and the second riser comprising a first end, a second end, and a taper formed from the first end to the second end, wherein
   the first end of the first riser and the first end of the second riser are closer together than the second end of the first riser and the second end of the second riser such that the first riser and the second riser are disposed at an acute angle relative to one another, and
   the first end of the first riser is disposed closer to the top edge of the board than the first end of the second riser defining a gap between the first ends such that the first riser and the second riser form an offset V-shape.

2. The therapeutic device of claim 1, wherein the first end of the first riser and the first end of the second riser are disposed near the top edge.

3. The therapeutic device of claim 2, wherein the upper surface is beveled towards the bottom edge.

4. The therapeutic device of claim 2, wherein at least one handle aperture is formed through the board near the bottom edge.

5. The therapeutic device 1, further comprising mating connectors disposed on the board and the first and second risers releasably connecting the first and second risers to the board.

6. The therapeutic device of claim 5, wherein the mating connectors comprise a plurality of pegs formed to mate with a plurality of peg holes.

7. The therapeutic device of claim 1, wherein a distance between the first ends of the first and second risers and the top edge is adjustable.

8. The therapeutic device of claim 1, further comprising a first spacer and a second spacer operable to adjust a height of the first riser and the second riser.

9. A therapeutic device comprising:
a board having an upper surface, a lower surface opposite the upper surface, and a perimeter comprising a top edge and a bottom edge opposite the top edge; and
a first riser and a second riser releasably secured to the upper surface of the board side by side, each of the first riser and the second riser comprising a first end, a second end, and a taper formed from the first end to the second end, wherein
the first end of the first riser and the first end of the second riser are closer together than the second end of the first riser and the second end of the second riser such that the first riser and the second riser are disposed at an acute angle relative to one another, and
a distance between the first ends and the top edge is adjustable between a first position and a second position, wherein the first position comprises the first end of the first riser and the first end of the second riser equidistant from the top edge of the board forming a V-shape and the second position comprises the first end of the first riser disposed closer to the top edge of the board than the first end of the second riser forming an offset V-shape.

* * * * *